(12) United States Patent
Anthis et al.

(10) Patent No.: US 9,580,799 B2
(45) Date of Patent: Feb. 28, 2017

(54) NITROGEN-CONTAINING LIGANDS AND THEIR USE IN ATOMIC LAYER DEPOSITION METHODS

(71) Applicant: Applied Materials, Inc., Santa Clara, CA (US)

(72) Inventors: Jeffrey W. Anthis, San Jose, CA (US); David Thompson, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 35 days.

(21) Appl. No.: 14/134,658

(22) Filed: Dec. 19, 2013

(65) Prior Publication Data

US 2014/0102365 A1    Apr. 17, 2014

Related U.S. Application Data

(62) Division of application No. 13/189,647, filed on Jul. 25, 2011, now Pat. No. 8,632,853.

(60) Provisional application No. 61/407,973, filed on Oct. 29, 2010.

(51) Int. Cl.

| | |
|---|---|
| *C07F 15/00* | (2006.01) |
| *C07D 207/335* | (2006.01) |
| *C23C 16/18* | (2006.01) |
| *C07D 213/36* | (2006.01) |
| *C23C 16/455* | (2006.01) |
| *C07D 213/38* | (2006.01) |
| *C07F 1/00* | (2006.01) |
| *C07F 1/08* | (2006.01) |
| *C07F 5/02* | (2006.01) |
| *C07F 5/06* | (2006.01) |
| *C07F 7/00* | (2006.01) |
| *C07F 7/28* | (2006.01) |
| *C07F 9/00* | (2006.01) |
| *C07F 11/00* | (2006.01) |
| *C07F 13/00* | (2006.01) |

(52) U.S. Cl.
CPC .......... *C23C 16/18* (2013.01); *C07D 207/335* (2013.01); *C07D 213/36* (2013.01); *C07D 213/38* (2013.01); *C07F 1/005* (2013.01); *C07F 1/08* (2013.01); *C07F 5/022* (2013.01); *C07F 5/069* (2013.01); *C07F 7/006* (2013.01); *C07F 7/28* (2013.01); *C07F 9/005* (2013.01); *C07F 11/005* (2013.01); *C07F 13/005* (2013.01); *C07F 15/004* (2013.01); *C07F 15/008* (2013.01); *C07F 15/0053* (2013.01); *C07F 15/0066* (2013.01); *C07F 15/0093* (2013.01); *C23C 16/45553* (2013.01)

(58) Field of Classification Search
USPC .................................................. 548/402, 561
See application file for complete search history.

(56) References Cited

U.S. PATENT DOCUMENTS

| | | | |
|---|---|---|---|
| 6,284,698 | B1 | 9/2001 | Chen et al. |
| 6,984,591 | B1 | 1/2006 | Buchanan et al. |
| 7,064,224 | B1 | 6/2006 | Lei et al. |
| 7,393,785 | B2 | 7/2008 | Uhlenbrock et al. |
| 2001/0046558 | A1 | 11/2001 | Kim et al. |
| 2004/0215030 | A1 | 10/2004 | Norman |
| 2006/0045968 | A1 | 3/2006 | Metz et al. |
| 2008/0209876 | A1 | 9/2008 | Miller |
| 2009/0056994 | A1 | 3/2009 | Kuhr et al. |
| 2010/0085801 | A1 | 4/2010 | Sorenson et al. |
| 2012/0231164 | A1 | 9/2012 | Thompson et al. |

FOREIGN PATENT DOCUMENTS

| | | |
|---|---|---|
| KR | 10-20001-0106023 | 11/2001 |
| WO | WO 2005/042545 | 5/2005 |

OTHER PUBLICATIONS

Bachman, G.B. et al.: The condensation of aldehydes and amines with nitrogenous five-atom ring systems. J. Am. Chem. Soc., vol. 68, pp. 2496-2499, 1946.*
Huang, J-H. et al.: Synthesis and characterization of organoaluminium complexes containing bi-ot tridentate-substituted pyrrole ligands. Organometallics, vol. 20, pp. 2647-2650, 2001.*
Lien, Y-L. et al.: Anew type of asymmetric tridentate pyrrolyl-linked pincer ligand and its aluminium dihydride complexes. Inorg. Chem., vol. 49, pp. 136-143, 2010.*
Hsieh, C-C. et al.: Synthesis and characterization of Nickel(II)complex containing 2-(t-butylaminomethyl)pyrrole. J. of the Chinese Chem. Soc., vol. 56, pp. 435-442, 2009.*
Non-Final Office Action in U.S. Appl. No. 13/189,647, dated Jun. 4, 2013, 12 pages.
PCT International Search Report and Written Opinion in PCT/US2011/045200, dated Mar. 15, 2012, 8 pages.
Banerjee, Sanjukta et al., Titanium-catalyzed iminohydrazination of alkynes, *Journal of Organometallic Chemistry*, 690 2005, 5066-5077.
Cao, Changsheng et al., A Titanium-Catalyzed Three-Component Coupling to Generate a,b—Unsaturaged b—Iminoamines, *J. Am. Chem. Soc.*, 125 2003, 2880-1881.
Csok, Zsolt et al., Nickel Complexes of a Pincer $NN_2$ Ligand: Multiple Carbon-Chloride Activation of $CH_2Cl_2$ and $CHCl_3$ Leads to Selective Carbon-Carbon Bond Formation, *J. Am. Chem. Soc.*, 130 2008, 8156-8157.
Hetterscheid, Dennis G. et al., Hydrogen-Atom Transfer in Open-Shell Organometallic Chemistry: The Reactivity of Rhll(cod) and Irll(cod) Radicals, *Chemistry A European Journal*, 13 2007, 3386-3405.
Li, Yahong et al., Synthesis and Structure of (Triphenylsilyl) imido Complexes of Titanium and Zirconium, *Organometallics*, 24 2005, 3272-3278.
Pohl, U. W. et al., Synthesis and properties of zinc-nitrogen compounds for the Movpe of p-type ZnSe, *Journal of Crystal Growth* 170 1997, 144-148.
Trepanier, Steven J. et al., Syntheses and Structures of Alkylaluminum Compleses with a Tridentate Amido Ligand,
(Continued)

*Primary Examiner* — Charanjit Aulakh
(74) *Attorney, Agent, or Firm* — Servilla Whitney LLC

(57) ABSTRACT

Methods for deposition of elemental metal films on surfaces using metal coordination complexes comprising nitrogen-containing ligands are provided. Also provided are nitrogen-containing ligands useful in the methods of the invention and metal coordination complexes comprising these ligands.

7 Claims, 4 Drawing Sheets

(56) References Cited

OTHER PUBLICATIONS $Al(CH_3)_2(Et_2NCH_2CH_2NCH_2CH_2NEt_2)$ and $Al_3(CH_3)_8(Et_2NCH_2CH_2NCH_2CH_2NEt_2)$, *Organometallics*, 13 1994, 2213-2217.
Vechorkin, Oleg et al., The Nickel/Copper-Catalyzed Direct Alkylation of Heterocyclic C—H Bonds, *Angew. Chem. Int. Ed.*, 49 2010, 3061-3064.
Wills, A. R. et al., New Organometallic Dialkylamido Complexes. X-Ray Crystal Structure of $Ph_2VN(CH_2CH_2NEt_2)_2$, *Polyhedron*, vol. 8, No. 11 1989, 1457-1459.

\* cited by examiner

NITROGEN-CONTAINING LIGANDS AND THEIR USE IN ATOMIC LAYER DEPOSITION METHODS

CROSS-REFERENCE TO RELATED APPLICATIONS

This application is a divisional application of U.S. Ser. No. 13/189,647, filed Jul. 25, 2011, which claims priority to U.S. Provisional Application No. 61/407,973, filed Oct. 29, 2010, the contents of both of which are hereby incorporated by reference in their entirety.

TECHNICAL FIELD

The present invention relates generally to methods of depositing thin films of elemental metal and to metal coordination complexes useful in such methods.

In particular, the invention relates to coordination complexes of metal cations with multidentate nitrogen-containing ligands and their use in atomic layer deposition processes.

BACKGROUND

Deposition of thin films on a substrate surface is an important process in a variety of industries including semiconductor processing, diffusion barrier coatings and dielectrics for magnetic read/write heads. In the semiconductor industry, in particular, miniaturization requires atomic level control of thin film deposition to produce conformal coatings on high aspect structures. One method for deposition of thin films with atomic layer control and conformal deposition is atomic layer deposition (ALD), which employs sequential, self-limiting surface reactions to form layers of precise thickness controlled at the Ångstrom or monolayer level. Most ALD processes are based on binary reaction sequences which deposit a binary compound film. Each of the two surface reactions occurs sequentially and because they are self-limiting a thin film can be deposited with atomic level control. Because the surface reactions are sequential, the two gas phase reactants are not in contact and possible gas phase reactions that may form and deposit particles are limited. The self-limiting nature of the surface reactions also allows the reaction to be driven to completion during every reaction cycle, resulting in films that are continuous and pinhole-free.

ALD has been used to deposit metals and metal compounds on substrate surfaces. $Al_2O_3$ deposition is an example of a typical ALD process illustrating the sequential and self-limiting reactions characteristic of ALD. $Al_2O_3$ ALD conventionally uses trimethylaluminum (TMA, often referred to as reaction "A" or the "A" precursor) and $H_2O$ (often referred to as the "B" reaction or the "B" precursor). In step A of the binary reaction, hydroxyl surface species react with vapor phase TMA to produce surface-bound $AlOAl(CH_3)_2$ and $CH_4$ in the gas phase. This reaction is self-limited by the number of reactive sites on the surface. In step B of the binary reaction, $AlCH_3$ of the surface-bound compound reacts with vapor phase $H_2O$ to produce AlOH bound to the surface and $CH_4$ in the gas phase. This reaction is self-limited by the finite number of available reactive sites on surface-bound $AlOAl(CH_3)_2$. Subsequent cycles of A and B, purging gas phase reaction products and unreacted vapor phase precursors between reactions and between reaction cycles, produces $Al_2O_3$ growth in an essentially linear fashion to obtain the desired film thickness.

While perfectly saturated monolayers are desired, this goal is very difficult to achieve in practice. The typical approach to further ALD development has been to determine whether or not currently available chemistries are suitable for ALD. Chemistries which have been explored for use in ALD processes include metal halides, metal alkyls, metal alkoxides, beta-diketonates, amides, imido/amido complexes amidinates, cyclopentadienyl complexes and mixed systems of the foregoing compounds. In addition, prior art processes for ALD have been most effective for deposition of metal oxide and metal nitride films. Although a few processes have been developed that are effective for deposition of elemental ruthenium and other late transition metals, in general ALD processes for deposition of pure metal have not been sufficiently successful to be adopted commercially. There is a need for new deposition chemistries that are commercially viable, particularly in the area of elemental metal films. The present invention addresses this problem by providing novel chemistries which are specifically designed and optimized to take advantage of the atomic layer deposition process.

SUMMARY

In one embodiment, the present invention provides methods for producing thin films of elemental metal on a substrate using metal coordination complexes as source material, wherein the coordinating ligand is a nitrogen-containing compound. The thin films may be produced using atomic layer deposition (ALD) processes, including plasma enhanced atomic layer deposition (PEALD) processes. In addition, plasma and thermal ALD processes are both applicable to the methods of the invention.

In an alternative embodiment, the method for producing elemental metal thin films using metal coordination complexes with nitrogen-containing ligands is a chemical vapor deposition (CVD) process.

In one embodiment of the invention, the metal coordination complexes used in the methods of the invention comprise at least one multidentate nitrogen-containing ligand. In a specific embodiment the ligand is tridentate. In a further specific embodiment the metal cation of the coordination complex is coordinated with two tridentate nitrogen-containing ligands, which may be the same (homoleptic) or different (heteroleptic). In an alternative embodiment, the metal coordination complexes useful in the methods of the invention are heteroleptic complexes comprising a single tridentate bisamineazaallylic ligand coordinated with the metal cation and the metal cation is additionally coordinated to at least one neutral or anionic ligand such as halogen (such as Cl), alkyl (such as $C_{1-3}$ alkyl), amido and imido; or to at least one mixed ligand other than an NNN ligand, such as amidinate, amido-amino and pyrrolyl-amino.

DETAILED DESCRIPTION

Figure 1A:
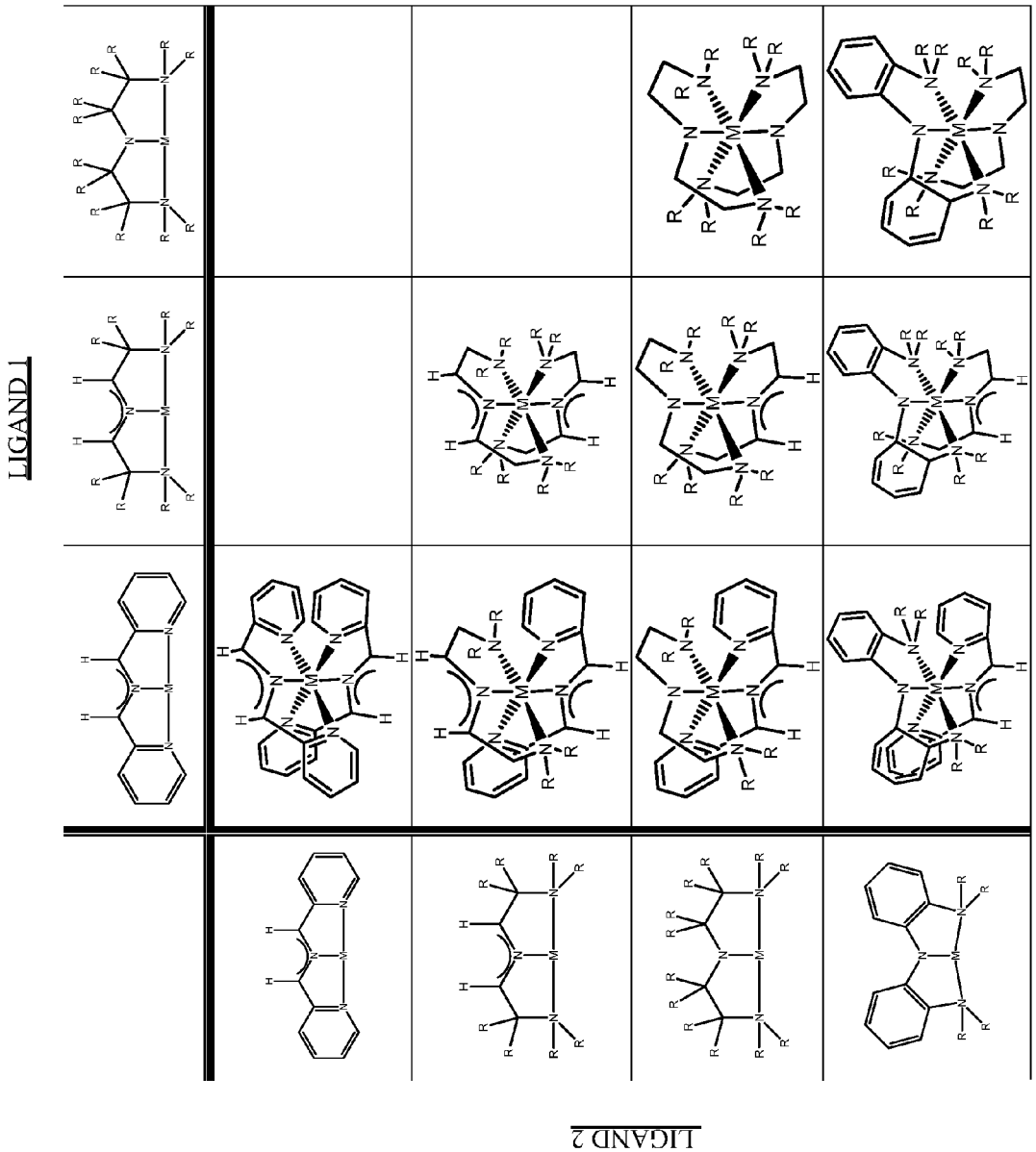
FIG. 1A, FIG. 1B and FIG. 1C are tables illustrating various exemplary NNN ligands and combinations of these NNN ligands in metal coordination complexes useful in the invention. The table includes the bisamineazaallylic ligands disclosed in the provisional US patent application filed by Applicants on even date herewith, as the ligands of that invention and the ligands of this invention may be combined in heteroleptic bis(NNN ligand) metal coordination complexes for use in thin layer metal deposition processes.
Figure 1B:
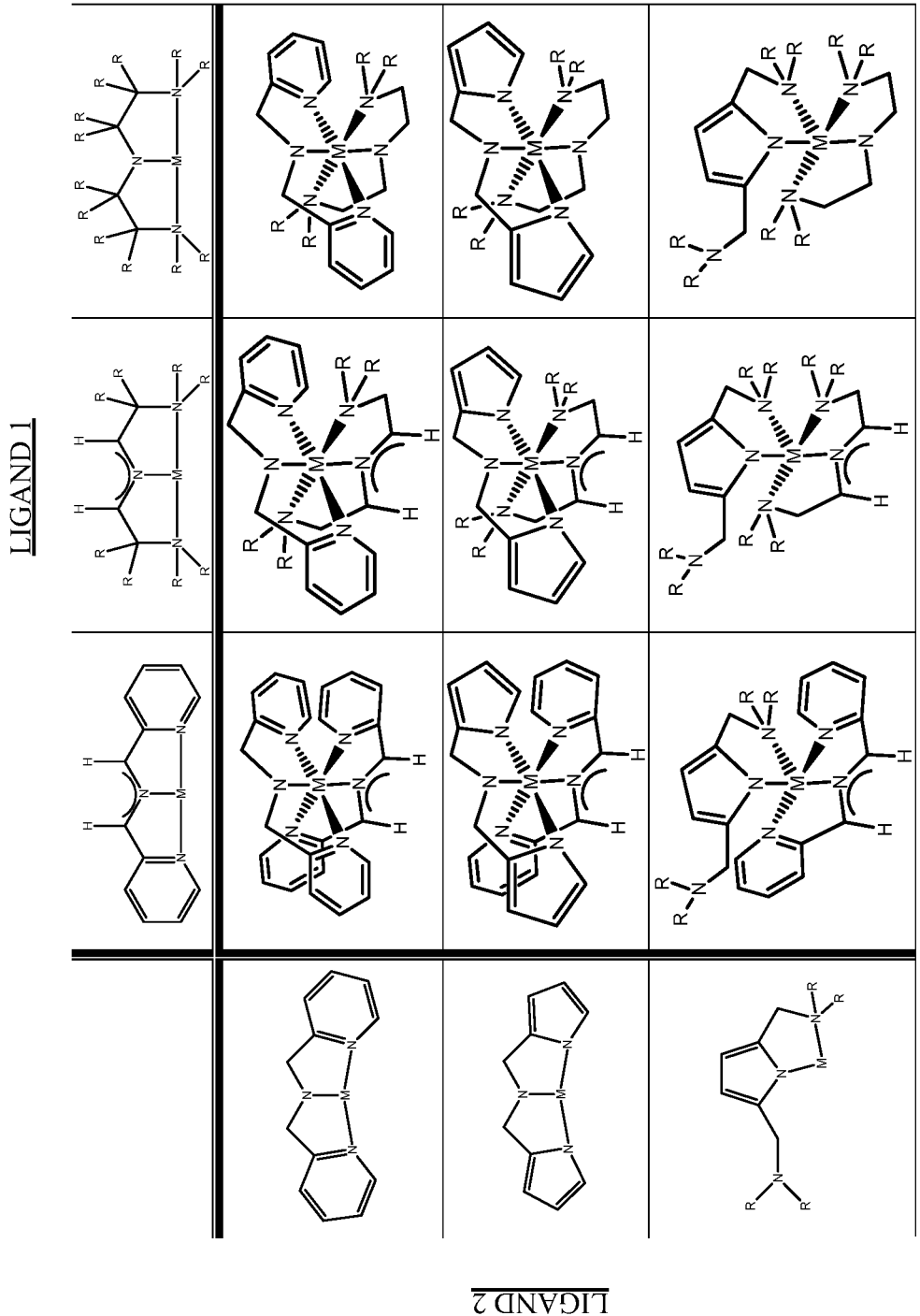
Figure 1C:
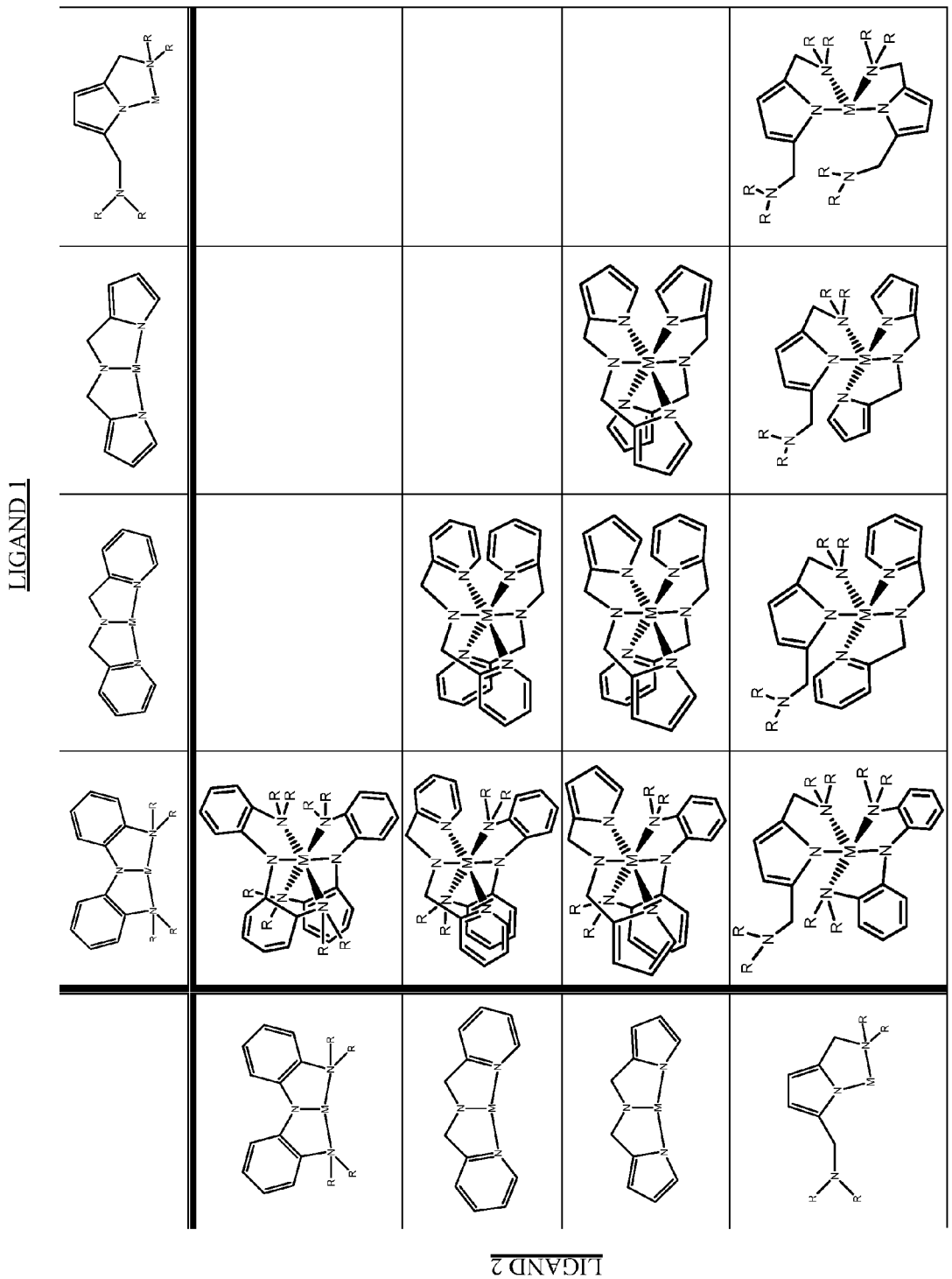

Before describing several exemplary embodiments of the invention, it is to be understood that the invention is not limited to the details of construction or process steps set forth in the following description. The invention is capable of other embodiments and of being practiced or being carried out in various ways. It is also to be understood that the complexes and ligands of the present invention may be illustrated herein using structural formulas which have a particular stereochemistry. These illustrations are intended as examples only and are not to be construed as limiting the disclosed structure to any particular stereochemistry. Rather, the illustrated structures are intended to encompass all such complexes and ligands having the indicated chemical formula.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

L, as used in the formulas disclosed herein, represents a ligand selected from the group consisting of neutral ligands ($L_{neutral}$), anionic ligands ($L_{anionic}$) and mixed ligands ($L_{mixed}$). Examples of neutral ligand molecules include no ligand, carbonyl, amino, bis-(pyridyl) and diamine; examples of anionic ligands include halogen (such as Cl), alkyl (such as $C_{1-3}$ alkyl), amido, aminomethyl and imido; and examples of mixed ligands include the NNN ligands of the type disclosed herein, amidinate, amido-amino, aminomethyl and pyrrolyl-amino. As is understood in the art, L may be any combination of $L_{neutral}$, $L_{anionic}$ and $L_{mixed}$ depending on the oxidation state of M.

The term "metal coordination complex" as used herein includes metal chelate complexes wherein a metal ion is coordinated with one or more polydentate ligands and metal coordination complexes wherein a metal ion is coordinated with one or more monodentate ligands. As will be discussed in more detail below, the metal complexes of the invention may consist only of chelating ligands or they may comprise both chelating ligands and coordinating ligands. The term "metal coordination complex" refers to both types of metal complex. The chelate effect of the polydentate ligand provides enhanced affinity for the metal ion in the complex as compared to the affinity of any nonchelating (monodentate) ligands in the complex for the same metal ion.

In general, ligands useful in the elemental metal thin layer deposition methods of the invention include multidentate (chelating) ligands which form at least one strong bond of covalent character to the metal center and at least one weaker bond to the metal center which involves dative bonding from the ligand. While not intending to be bound by theory, it is believed that the chelate effect helps to stabilize the metal-ligand precursor complex in the vapor phase while maintaining the ability to provide an active site for nucleation of the precursor on a surface.

In one embodiment of the invention, the nitrogen-containing ligand useful for forming the metal coordination complex may be a member of one of four groups of structurally related compounds. A first such group of ligands may be represented by formula $R_1R_2N$—$(CR)_x$—N—$(CR)_y$—$NR_7R_8$, wherein each R is independently hydrogen, $C_{1-6}$ alkyl, acyl, aldehyde, keto or $C_{2-4}$ alkenyl and x and y are independently 2-6. As an example, the first group of ligands may be represented by formula (I):

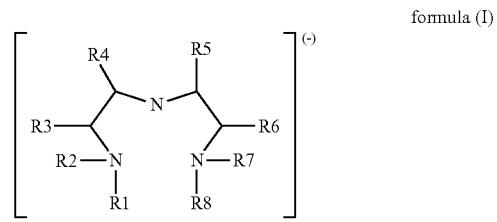

formula (I)

wherein each R is independently hydrogen, $C_{1-6}$ alkyl, acyl, aldehyde, keto or $C_{2-4}$ alkenyl and x and y are independently 2-6. The ligand represented by formula (I) may also be represented in its protonated form by formula (I'):

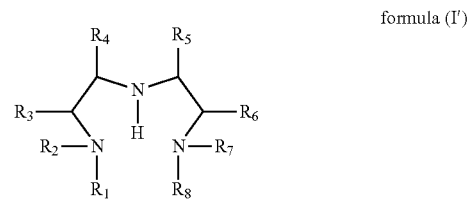

formula (I')

wherein each R is defined as above with respect to formula (I).

A specific example of a ligand belonging to the first group is a tridentate compound wherein $R_1$, $R_2$, $R_7$ and $R_8$ are each ethyl (Et) and each of $R_3$-$R_6$ is independently hydrogen, $C_{1-6}$ alkyl, acyl, aldehyde, keto or $C_{2-4}$ alkenyl. In a further specific embodiment each of $R_{3-6}$ is hydrogen (S. J. Trepanier, et al (1994) *Organometallics* 13:2213-2217; U. W. Pohl, et al. (1997) *J. Crystal Growth* 170:144-148; A. R. Wills, et al. (1989) *Polyhedron* 8:1457-1459).

This group of ligands, when complexed with a transition metal cation or a boron group cation M, is represented by formula (II):

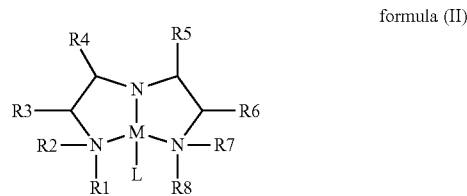

formula (II)

wherein each R is as defined with respect to formula (I), M is a transition metal or boron group cation and L is one or more ligands as defined above as appropriate for the oxidation state of the selected M.

A second group of structurally related ligands useful in the metal coordination complexes of invention may be represented by formula R$_1$R$_2$N—Ar$_1$—NH—Ar$_2$—NR$_3$R$_4$, wherein each R is independently hydrogen, C$_{1-6}$ alkyl, acyl, aldehyde, keto or C$_{2-4}$ alkenyl, and Ar$_1$ and Ar$_2$ are aromatic hydrocarbon moieties which may be the same or different.

As an example, when Ar$_1$ and Ar$_2$ are pyridyl, the second group of ligands may be represented by structural formula (III):

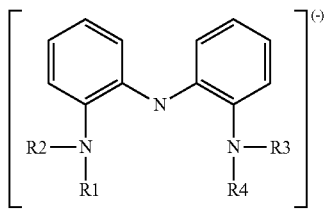

formula (III)

wherein each R is independently hydrogen, C$_{1-6}$ alkyl, acyl, aldehyde, keto or C$_{2-4}$ alkenyl. The ligand represented by formula (III) may also be represented in its protonated form by formula (III'):

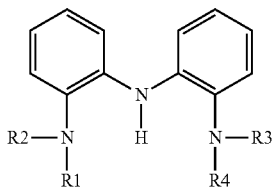

formula (III')

wherein each R is as defined above with respect to formula (III).

A specific embodiment of a ligand belonging to the second structurally related group is a tridentate compound wherein each of R$_{1-4}$ is methyl (Me) (Z. Csok, et al. (2008) *JACS* 130:8156-8157; O. Vechorkin, et al. (2010) *Angew. Chem. Int. Ed.* 49:3061-3064).

This group of ligands, when complexed with a transition metal cation or a boron group cation M, is represented by formula (IV):

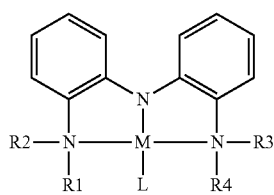

formula (IV)

wherein each R is as defined with respect to formula (III). M is a transition metal or boron group cation and L is one or more ligands as defined above as appropriate for the oxidation state of the selected M. As an example, each of R$_{1-4}$ may be methyl (Me). It is to be understood that the pyridyl moieties of formula (IV) may be substituted with any aromatic hydrocarbon moiety.

A third group of structurally related ligands useful in the invention may be represented by formula R$_1$R$_2$N—(CR$_3$R$_4$)$_x$—N$_{Ar}$—(CR$_5$R$_6$)$_y$—NR$_7$R$_8$, wherein each R is independently hydrogen, C$_{1-6}$ alkyl, acyl, aldehyde, keto or C$_{2-4}$ alkenyl, and N$_{Ar}$ is a heterocyclic aromatic moiety wherein the heteroatom is N. An example of the third group of ligands may be represented by structural formula (V):

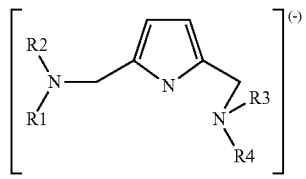

formula (V)

wherein each R is independently hydrogen, C$_{1-6}$ alkyl, acyl, aldehyde, keto or C$_{2-4}$ alkenyl. The ligand represented by formula (V) may also be represented in its protonated form by formula (V'):

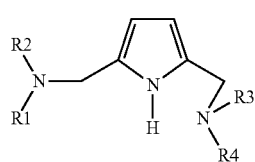

formula (V')

wherein each R is as defined above with respect to formula (V).

A specific embodiment of a ligand according to formula (V) is a tridentate compound wherein each of R$_{1-4}$ is Me (Y. Li, et al. (2005) *Organometallics* 24:3272-3278; S. Banerjee, et al. (2005) *J. Organometallic Chem.* 690:5066-5077).

The formula (V) ligand, when complexed with a transition metal cation or a boron group cation M, is represented by formula (VI):

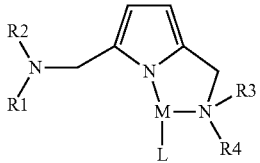

formula (VI)

wherein each R is as defined with respect to formula (V), M is a transition metal or boron group cation and L is one or more ligands as defined above as appropriate for the oxidation state of the selected M. As an example, R may be Me (methyl).

A fourth group of structurally related ligands useful in the invention may be represented by formula N$_{Ar1}$—(CR$_1$R$_2$)$_x$—NR$_5$—(CR$_3$R$_4$)$_y$—N$_{Ar2}$, wherein each R is independently hydrogen, C$_{1-6}$ alkyl, acyl, aldehyde, keto or C$_{2-4}$ alkenyl, and N$_{Ar1}$ and N$_{Ar2}$ may be the same or different and are heterocyclic aromatic moieties wherein the heteroatom is N. For example, N$_{Ar1}$ and N$_{Ar2}$ may be pyrrolyl. In an example of a ligand in the third group of ligands N$_{Ar1}$ and N$_{Ar2}$ are pyrrolyl and each R is H, may be represented by formula (VII):

formula (VII)

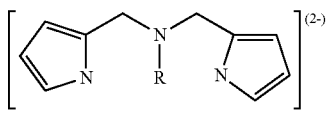

wherein R is hydrogen, $C_{1-6}$ alkyl, acyl, aldehyde, keto or $C_{2-4}$ alkenyl (C. Cao, et al. (2003) *J. Am. Chem. Soc.* 125:2880-2881; S. Banerjee, et al. (2005) *J. Organometallic Chem.* 690:5066-5077). The ligand represented by formula (VII) may also be represented in its protonated form as formula (VII'):

formula (VII')

wherein R is as defined above with respect to formula (VII).

In an alternative embodiment, either pyrrole moiety or both pyrrole moieties may be replaced with pyridyl in formula (VII). As an example, this may result in a ligand represented by formula (VIII) in which $R_5$ is absent and the central nitrogen is anionic:

formula (VIII)

The ligand represented by formula VIII may also be represented in its protonated form by formula (VIII'):

formula (VIII')

Pyrrolyl members of the fourth group of ligands, when complexed with a transition metal cation or a boron group cation M, are represented by formula (IX):

formula (IX)

wherein M is a transition metal or boron group cation, R is hydrogen, $C_{1-6}$ alkyl, acyl, aldehyde, keto or $C_{2-4}$ alkenyl, and L is one or more ligands as defined above as appropriate for the oxidation state of the selected M. Other ligands within the definition of the fourth group of structurally related ligands may be substituted for the exemplary pyrrolyl ligand in the transition metal complexes.

In an alternative embodiment, either pyrrole moiety or both pyrrole moieties may be replaced with pyridyl in the ligand of the metal coordination complex. As an example, the complex wherein both $N_{Ar1}$ and $N_{Ar2}$ are pyridyl and each R is H is represented by formula (X):

formula (X)

The nitrogen-containing ligands of the first, second and third structural groups described above chelate the metal cation via the end-group nitrogens and the anionic central nitrogen. The pendant nitrogen atoms are generally in trans conformation. In this situation, the dative bonds may be longer and weaker than the central metal-to-nitrogen bond and therefore may have greater potential to release from the metal center. This can create a nucleation site on the metal center which is available for reaction with a substrate surface in an ALD process. While not intending to be bound by theory, it is believed that the chelate effect helps to stabilize the metal-ligand precursor complex in the vapor phase while retaining the ability to provide an active site for nucleation of the precursor on a surface.

When the central anionic nitrogen atom is present as a conjugated pyrrolyl moiety it is typically bound eta-1 to the metal center. When one of the metal to dative nitrogen bonds is broken to create a nucleation site it becomes possible for the pyrrolyl fragment to slip into an eta-5 bonding mode which may contribute to stabilization of the metal center. It may also be possible for the pyrrolyl fragment to slip into an eta-5 bonding mode without dissociation of the pendant amine.

The nitrogen-containing ligands of the fourth structural group described above form two covalent M-N bonds via the anionic end-group nitrogens and one dative bond via the central nitrogen with the metal cation. This type of metal coordination complex precursor is also prevented from decomposing in ALD processes, but the two stronger bonds at either end stabilize the complex while the nucleation site forms at the center at the dative nitrogen.

The ligands of the fourth structural group have two outer anionic nitrogen atoms and therefore oxidize the metal center by two electrons, resulting in bonding in a facial arrangement. In this geometry the metal to central dative nitrogen bond is still capable of breaking to create a nucleation site. These ligands, however, are likely to be most useful for complexing earlier transition metals which require higher oxidation states.

Figure 2:
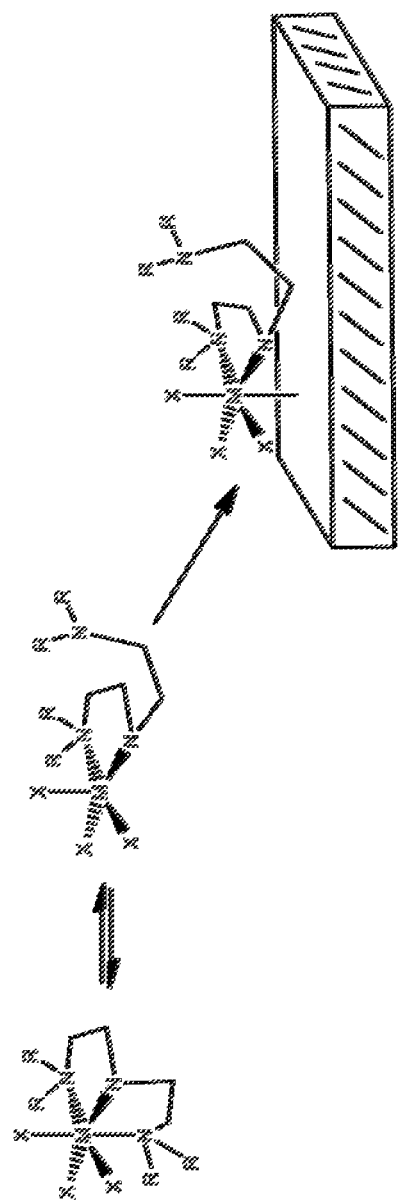
FIG. 2 is an illustration of an ALD process using a representative metal coordination complex according to the invention.

In one embodiment of the invention the process for preparing thin films of elemental metal is an ALD process. In the illustrative example of such a process shown in FIG. 2, the metal coordination complex used is represented by formula (II) wherein L consists of three ligands each of which is independently anionic, neutral or mixed but which are not NNN ligands (collectively represented by "X" in FIG. 2). As illustrated, the metal coordination complex is vaporized, optionally in a mixture with an inert carrier gas, and flowed in the vapor phase to a substrate within a deposition chamber (not shown). The substrate has a surface that is appropriate for adsorption of the metal coordination complex to the surface via the metal ion when one of the pendant amines dissociates from the complex, exposing an active site for bonding with the surface. In this example the surface for adsorption may be bare metal. The surface is exposed to the nitrogen-containing metal coordination complex for sufficient time to permit adsorption of the complex in a layer on the surface. This first layer on the substrate comprises M in a coordination complex with L and the NNN ligand. Following formation of the first layer, precursor gas containing the unreacted nitrogen-containing metal coordination complex is purged from the deposition chamber using an inert gas. A reducing gas is then flowed into the deposition chamber to reduce the bond(s) between the metal, L and the remaining two nitrogens of the complex, releasing the L and NNN ligands from the metal center and leaving an atomic layer of elemental metal on the substrate.

Optionally, a second atomic layer of elemental metal may be formed on the first atomic layer by repeating the steps of the reaction cycle. Hydrogen remaining from the preceding reduction reaction is purged from the deposition chamber using an inert gas and a metal coordination complex in vapor phase is again flowed into the chamber into contact with the metal film on the substrate surface. An exchange reaction occurs between the nitrogen-containing metal coordination complex in the vapor phase and hydrogen atoms on the metal of the first atomic layer. This displaces one of the ligands from the vapor phase metal coordination complex and leaves the metal atom of the metal coordination complex bound to the metal atom of the first atomic layer. The reaction time, temperature and pressure are selected to create a metal-surface interaction and form a layer on the surface of the substrate. Unreacted vapor phase metal coordination complex and released ligand are purged from the deposition chamber using an insert gas. A reducing gas is flowed into the deposition chamber to reduce the bond(s) between the metal and any remaining ligand(s), releasing the remaining ligand(s) from the metal center and producing a second atomic layer of elemental metal on the first atomic layer of elemental metal.

Additional repetitions of the deposition cycle may be used to build a layer of elemental metal of the desired thickness.

In an alternative aspect of the ALD deposition methods of the invention the substrate has a surface that is activated for reaction with the metal coordination complex to form a first layer on the substrate. A metal coordination complex according to the invention is vaporized and flowed in the vapor phase to a substrate within a deposition chamber. The reaction between the nitrogen-containing metal coordination complex and the surface may occur by an exchange reaction in which hydrogen atoms on the surface displace either one of the NNN ligands from the complex (if two or more NNN ligands are bound to the metal center) or one of the L ligands bound to the metal center (when one NNN ligand is bound to the metal center). The metal atom becomes bound to the surface. The reaction time, temperature and pressure are selected to create a metal-surface interaction and achieve a layer on the surface of the substrate. The first layer comprises the metal bound to the surface and coordinated with at least one ligand. Following formation of the first monolayer, precursor gas containing unreacted nitrogen-containing metal coordination complex and released ligand are purged from the deposition chamber using an inert gas. A reducing gas is then flowed into the deposition chamber to reduce the remaining bond(s) between the metal and the ligand(s) of the coordination complex, releasing the remaining ligand(s) from the metal center and leaving an atomic layer of elemental metal on the substrate.

As in the adsorption ALD process discussed above, a second atomic layer of elemental metal may optionally be formed on the first atomic layer by repeating the steps of the reaction cycle. Hydrogen remaining from the preceding reduction reaction is purged from the deposition chamber using an inert gas and a metal coordination complex in vapor phase is again flowed into the chamber into contact with the metal film on the substrate surface. An exchange reaction occurs between the nitrogen-containing metal coordination complex in the vapor phase and hydrogen atoms on the metal of the first atomic layer. This displaces one of the ligands from the vapor phase metal coordination complex, reducing the displaced ligand and leaving the metal atom of the metal coordination complex bound to the metal atom of the first atomic layer. The reaction time, temperature and pressure are selected to achieve a uniform layer on the surface of the substrate. Unreacted vapor phase metal coordination complex and released H-ligand are purged from the deposition chamber using an insert gas. A reducing gas is flowed into the deposition chamber to reduce the bond(s) between the metal and any remaining ligand(s), releasing the remaining ligand(s) from the metal center and producing a second uniform atomic layer of elemental metal on the first atomic layer of elemental metal.

Additional repetitions of the deposition cycle may be used to build a layer of elemental metal of the desired thickness.

The substrate for deposition of the elemental thin layer films may be any substrate suitable for conformal film coating in an ALD or CVD process. Such substrates include silicon, silica or coated silicon, metal, metal oxide and metal nitride. In one aspect of the invention, the substrate is a semiconductor substrate.

The nitrogen-containing metal coordination complexes useful in the methods of the invention include as the coordinated metal any of the transition metals (Groups 3-12 of the periodic table of the elements) and any of the boron group metals (Group 13 of the periodic table of the elements). Of these, copper, silver, gold, palladium, platinum, rhodium, iridium, tungsten, titanium, zirconium, hafnium, vanadium, niobium, tantalum, chromium, molybdenum, aluminum, manganese and ruthenium are of particular interest as elemental metal thin films and may be incorporated into the nitrogen-containing metal coordination complexes of the invention as is known in the art based on their oxidation states.

The reaction conditions for the ALD reaction will be selected based on the properties of the selected nitrogen-containing metal coordination complex. The deposition can be carried out at atmospheric pressure but is more commonly carried out at a reduced pressure. The vapor pressure of the metal coordination complex should be high enough to be practical in such applications. The substrate temperature should be low enough to keep the bonds between the metal atoms at the surface intact and to prevent thermal decomposition of gaseous reactants. However, the substrate temperature should also be high enough to keep the source materials (i.e., the reactants) in the gaseous phase and to provide sufficient activation energy for the surface reaction. The appropriate temperature depends on the specific nitrogen-containing metal coordination complex used and the pressure. The properties of a specific metal coordination complex for use in the ALD deposition methods of the invention can be evaluated using methods known in the art, allowing selection of appropriate temperature and pressure for the reaction. In general, lower molecular weight and the presence of functional groups that increase the rotational entropy of the ligand sphere result in a melting point that yields liquids at typical delivery temperatures and increased vapor pressure.

An optimized nitrogen-containing metal coordination complex for use in the deposition methods of the invention will have all of the requirements for sufficient vapor pressure, sufficient thermal stability at the selected substrate temperature and sufficient reactivity to produce a self-limiting reaction on the surface of the substrate without unwanted impurities in the thin film or condensation.

Sufficient vapor pressure ensures that molecules of the source compound are present at the substrate surface in sufficient concentration to enable a complete self-saturating reaction. Sufficient thermal stability ensures that the source compound will not be subject to the thermal decomposition which produces impurities in the thin film.

Any metal coordination complex represented by a transition metal or a boron group metal chelated with a ligand of formula $R_1R_2N$—$(CR)_x$—N—$(CR)_y$—$NR_7R_8$, formula $R_1R_2N$—$Ar_1$—$NH$-$Ar_2$—$NR_3R_4$, formula $R_1R_2N$—$(CR_3R_4)_x$—$N_{Ar}$—$(CR_5R_6)_y$—$NR_7R_8$, formula $N_{Ar1}$—$(CR_1R_2)_x$—$NR_5$—$(CR_3R_4)_y$—$N_{Ar2}$, including but not limited to complexes represented by formula (II), formula (IV), formula (VI), formula (VIII) and formula (VIII'), and having suitable vapor pressure properties may be used in the thin layer film deposition methods of the invention:

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A metal coordinating ligand having a formula

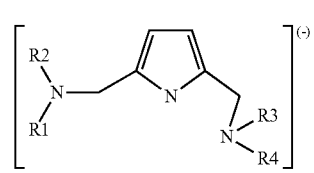

formula V or a protonated form thereof, wherein each R is independently $C_{1-6}$ acyl, aldehyde, keto or $C_{2-4}$ alkenyl.

2. An apparatus comprising:
   a deposition chamber; and
   the metal coordinating ligand of claim 1.

3. The apparatus of claim 2, wherein the metal coordinating ligand is in the vapor phase.

4. A metal coordination complex comprising a transition metal ion or a boron group ion M complexed with the metal coordinating ligand of claim 1.

5. The metal coordination complex of claim 4, wherein the transition metal ion or the boron group ion is selected from the group consisting of aluminum, titanium, tungsten, zirconium, vanadium, niobium, tantalum, chromium, molybdenum, palladium, platinum, rhodium, iridium, silver, gold, hafnium, manganese, ruthenium and copper.

6. An apparatus comprising:
   a deposition chamber; and
   the metal coordination complex of claim 4.

7. The apparatus of claim 6, wherein the metal coordination complex is in the vapor phase.

* * * * *